United States Patent [19]

Stewart et al.

[11] Patent Number: 5,328,831
[45] Date of Patent: Jul. 12, 1994

[54] SUBSTRATE COMPOSITION FOR SOLID PHASE UREASE IMMUNOASSAY

[75] Inventors: Thomas N. Stewart, Durham; Glenn P. Vonk, Fuquay-Varina; James P. Mapes, Raleigh, all of N.C.

[73] Assignee: Becton, Dickinson and Company, Franklin Lakes, N.J.

[21] Appl. No.: 851,602

[22] Filed: Mar. 16, 1992

Related U.S. Application Data

[62] Division of Ser. No. 528,526, May 25, 1990, Pat. No. 5,139,934.

[51] Int. Cl.⁵ .................. B12Q 1/58; C12Q 1/00; C12N 9/96
[52] U.S. Cl. .................. 435/12; 435/7.91; 435/188; 436/904
[58] Field of Search .................. 435/12, 7.91, 188; 436/904

[56] References Cited

U.S. PATENT DOCUMENTS 4,892,817  1/1990  Pawlak .................. 435/21
4,946,776  8/1990  Ritterband .................. 435/21

Primary Examiner—Michael G. Wityshyn
Assistant Examiner—Ralph Gitomer
Attorney, Agent, or Firm—Donna R. Fugit

[57] ABSTRACT

A substrate composition for use in a solid phase enzyme assay for urease or in a solid phase enzyme immunoassay which includes urease as a label. The substrate composition includes a compound converted by urease to ammonia and a pH dependent reducing agent which reduces a tetrazolium salt when the pH of the medium has been raised by the ammonia produced. The tetrazolium salt may optionally be included in the substrate composition. Reduction of the tetrazolium salt produces a colored insoluble formazan which precipitates on the solid phase as an indication of the presence of urease.

8 Claims, 1 Drawing Sheet

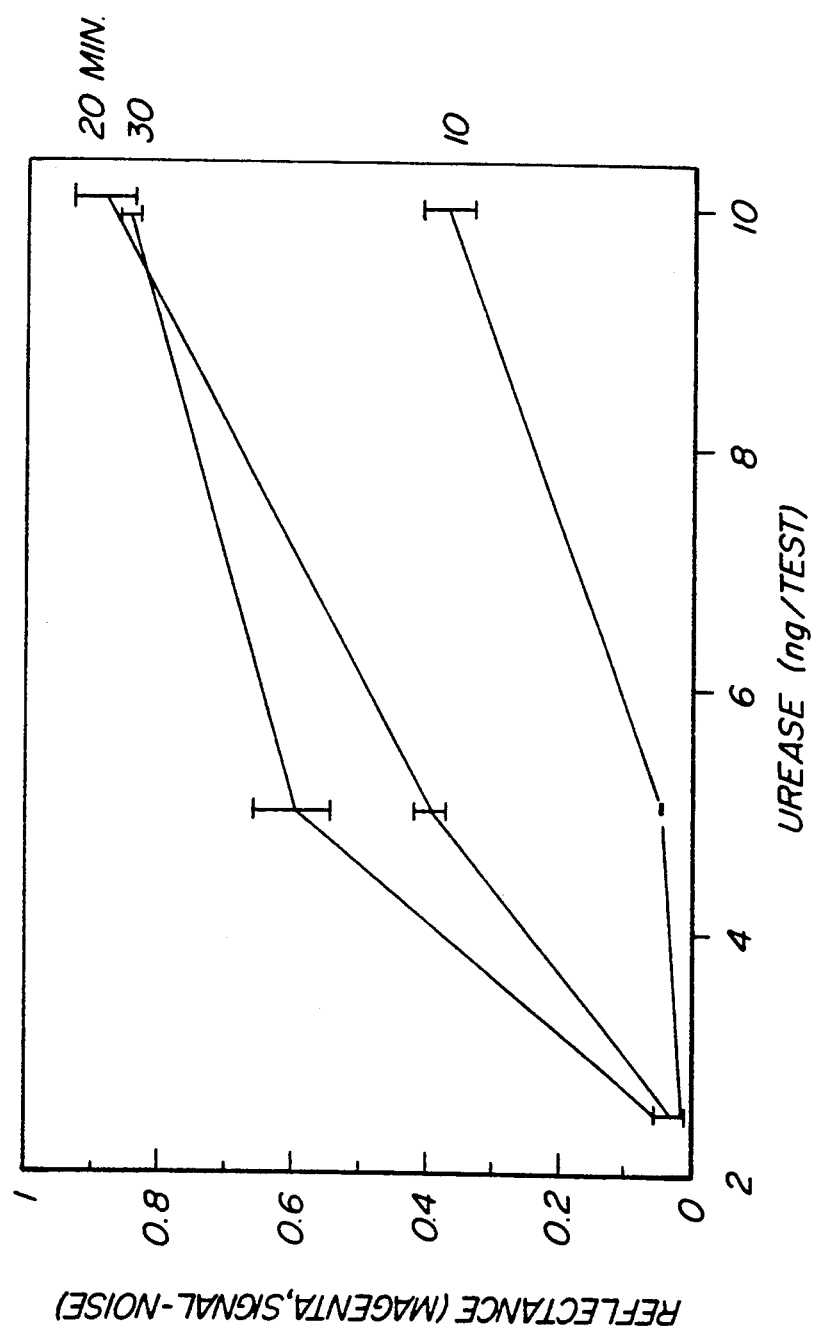

SUBSTRATE COMPOSITION FOR SOLID PHASE UREASE IMMUNOASSAY

This is a division of application Ser. No. 07/528,526, filed May 25, 1990, now U.S. Pat. No. 5,139,934.

BACKGROUND OF THE INVENTION

1. Field of the Invention

This invention relates to immunoassay for a ligand, and more particularly relates to membrane immunoassay and particular reagents useful therein.

2. Background of the Invention

Assay systems which are both rapid and sensitive have been developed to determine the concentration of a substance, generally referred to as the analyte, present in low concentration in a fluid sample. Immunoassays depend on the binding of an antigen or hapten to a specific antibody and have been particularly useful because they give high levels of specificity and sensitivity. These assays employ one of the above reagents in labeled form, the labeled reagent being referred to as the tracer.

Enzymes have often been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

A convenient format for EIA is solid phase immunoassay in which one of the assay reagents is immobilized on a solid support. The solid support may be in the form of a dipstick, the inside wall of a test tube or cuvette or the well of a microtiter plate. A particularly useful solid support is a microporous membrane.

Membrane immunoassay is often referred to as flow-through assay. Examples of flow-through EIA wherein flow is generated by capillary action are the assays described in U.S. Pat. No. 3,888,629 to Bagshaw, U.S. Pat. No. 4,246,339 to Cole et al. and U.S. Pat. No. 4,632,901 to Valkirs et al. U.S. Pat. No. 4,277,560 to Gray and U.S. Pat. No. 4,812,293 to McLaurin et al. are examples of flow-through assays using pressure and vacuum respectively.

In membrane EIA, any number of liquids may be caused to flow through the membrane to effect binding, separation and washing of assay components. The final step in most membrane EIA procedures is contacting a color developing reagent, such as a chromogen, with the membrane. The chromogen reacts with enzyme captured on the membrane to produce a colored product which may be detected as evidence of the presence of analyte or measured as evidence of the concentration of analyte. The colored product may be soluble, in which case it will pass through the membrane and be detected in the filtrate, or it may be insoluble and form a colored spot on the membrane.

The enzyme urease converts urea into carbon dioxide and ammonia. It has been developed as a label for solution immunoassay wherein a rise in pH of the assay medium due to the ammonia production is detected colorimetrically with an indicator such as bromcresol purple (Chandler et al., *Journal of Immunological Methods* 53,187 (1982); U.S. Pat. No. 4,590,157).

EIA in which urease is detected colorimetrically in solution by the Chandler et al. procedure provides an excellent visual readout because the detected product is deeply colored and water soluble. On the other hand, rapid diffusion due to the water solubility precludes deposition of the product as a spot on a solid phase, such as a dipstick or a membrane. This severely limits usefulness of urease in solid phase EIA procedures. There is a need for a urease substrate which would be converted to an insoluble product to be deposited on a solid phase. Such a substrate would greatly extend the usefulness of urease as an immunological label. The present invention provides such a substrate.

SUMMARY OF THE INVENTION

One aspect of the invention is a method for enzyme immunoassay of a ligand. A liquid sample suspected of containing the ligand is incubated with a solid support having affixed thereto a capture antiligand whereby the ligand is bound to the support. The support may then be contacted with a tracer comprising a detection antiligand conjugated to urease so that urease becomes affixed to the support. A substrate composition for the urease is then brought into contact with support. Urease converts a first component of the composition to ammonia. The ammonia raises the pH of the assay medium sufficiently to activate a second component of the composition, a pH dependent reducing agent. When activated, the reducing agent reduces a third component, a tetrazolium salt, to a colored insoluble formazan which precipitates as a detectable spot on the support.

A preferred support is a porous membrane which preferably is mounted in a suitable holder adjacent an absorbent pad. The pad causes liquids to flow through the membrane by capillary action.

The preferred ligand for assay is an antigen, most preferably a vital antigen, and the preferred capture antiligand is an antibody. The preferred tracer is a second antibody, referred to as the detection antibody, conjugated to urease. The preferred substrate composition includes urea as the ammonia generating compound and ascorbic acid as the reducing agent which reduces the tetrazolium salt when the liberated ammonia causes a rise in the pH.

Thus, the assay system of the invention provides significant improvement in immunoassay using urease as the label. First and foremost, the substrate composition provides a colored detectable product which precipitates on a solid support in contrast to all urease assays in the prior art which are solution assays. The color formed is stable and not reversible, so that the enzymatic reaction can be stopped with a wash solution without loss or change in the color. In contrast, urease assays of the prior art using pH indicators such as bromcresol purple or phenol red give reversible color changes. The invention takes advantage of the fast turnover rate of urease and overcomes the limitation in the prior art of solution assay, making possible commercial development of a urease assay by the far easier and more dependable solid phase format.

BRIEF DESCRIPTION OF THE DRAWING

The figure illustrates detection of urease activity by the method of the invention as a function of incubation time.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

One aspect of the present invention is a substrate composition which is converted by the urease to a colored insoluble product. A second aspect of the invention is a method for immunoassay of a ligand using urease as the label and the composition as substrate. The method takes advantage of the many attributes of urease as a label and at the same time overcomes the drawback which has heretofore prevented this enzyme from achieving widespread use in immunoassay.

The assay of the invention may be performed by any conventional solid phase technique in which the presence or absence of a ligand in a sample is detected by enzyme catalyzed conversion of a substrate to a colored product. For example, the assay of the invention may be performed by immunochromatography. In this procedure, a liquid phase containing ligand to be detected migrates by capillary action across a solid phase, such as a glassplate, having various assay components deposited on adjacent but separated zones thereof. Representative of this procedure are the assays disclosed in U.S. Pat. No. 4,740,468 to Weng et al. and U.S. Pat. No. 4,446,232 to Liotta.

Another suitable assay technique uses a dipstick. In this procedure, a solid phase, usually a glass plate having a binder containing a capture antibody thereon, is dipped alternately into the test liquid, liquids containing assay reagents and wash liquids. In the last dip, an enzyme captured on the dipstick in proportion to the concentration of ligand in the test liquid converts the substrate of the invention to a colored product which deposits on the dipstick and which is indicative of the presence of ligand.

While immunoassay for a ligand as described above is a preferred application of the invention, one skilled in the art will immediately recognize that the method may be used in an assay wherein the ligand may be a nucleic acid probe and the tracer may be a complementary strand of DNA or RNA conjugated to urease. Assay procedures having enzymes conjugated to DNA and RNA strands are well-known in the art.

A preferred assay technique is flow-through assay in which the solid phase is a porous membrane. The membrane may be positioned in any suitable assay device adapted for flow-through assay as known in the art. In preferred devices, flow of assay liquids is promoted by capillary action induced by a pad of absorbent material adjacent the membrane, and the membrane and absorbent pad are mounted in a suitable housing. Membrane flow-through assay and various devices therefor have been disclosed and several devices are commercially available.

The porous membrane may be of any material which does not interfere in any way with any other component or step of the assay. Suitable membranes are, for example, of glass fiber, polyvinylidene difluoride, polycarbonate, nitrocellulose and nylon. Such membranes are well-known in the art and many are commercially available from suppliers such as Pall (East Hills, N.Y.), Millipore (Bedford, Mass.) and Schleicher and Schuell (Keene, N.H.).

The ligand may be from any source, and may be an antigen, an antibody or a hapten. For example, the ligand may be an endocrine hormone, such as HCG or FSH, present in body fluid, or it may be isolated from a body fluid and subsequently introduced into a different liquid, such as buffer. In other cases, the ligand may be from a source other than a body fluid, as, for example, a culture of microorganisms such as Chlamydia or a cellular extract thereof. Antibodies, such as the antibody against Lyme disease, may be assayed, or the ligand may be a hapten such as a therapeutic drug or a drug of abuse.

Preferred ligands are antigens, most preferably viral antigens present in a body fluid, such as Adenovirus, Parainfluenza 3 virus and, most preferably, Herpes simplex virus (HSV), Respiratory syncytial virus (RSV), and Influenza A (Flu A). The invention will hereinafter be described generically in terms of the preferred membrane assay.

The membrane may be coated with an antiligand specific for the ligand. Thus, in the case where the ligand is the preferred viral antigen, the antiligand may be an antibody which binds specifically to the antigen and thereby captures the antigen on the membrane. This reagent is hereinafter referred to as the capture antibody. The membrane may be further coated with an inert protein to fill any binding sites on the membrane not occupied by the capture antibody. (In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.) Representative nonlimiting examples of suitable inert proteins are casein and albumin, although others will be evident to those skilled in the art.

If the ligand is a hapten, it may be necessary to conjugate the hapten to a protein in order to raise a suitable anti-hapten capture antibody. Such procedures are well-known in the art of hapten immunoassay, and further details with respect to this aspect of the invention are not needed for a complete understanding of the invention.

Coating of the membrane with either or both of the capture antibody or the inert protein may be carried out by any suitable method, preferably by incubating the membrane with a solution of the antibody and/or inert protein whereby the protein is physically absorbed into the polymeric matrix of the surface of the membrane. Coating procedures are wholly conventional in the art.

The membrane may be incubated with the sample suspected of containing the ligand in order to bind the ligand to the antiligand coated onto the membrane. Preferably the sample is applied to the coated membrane and allowed to pass through the membrane in a transient, flow-through format for about 1 to 15, preferably about 5 minutes at a temperature of about 0° to 50° C., preferably about ambient temperature. By this procedure, antigen in the sample is captured on the membrane in proportion to its concentration in the sample. In addition, it has been found that viral antigen is absorbed preferentially even when the sample contains a large excess of extraneous protein, such as is the case when the sample is a body fluid.

In an alternate embodiment of the invention, the membrane may be coated with the inert protein and the antigen absorbed directly onto this surface and the assay performed without a capture antibody. Flow-through immunoassay absent a capture antibody is disclosed in copending application Ser. No. 272,380, filed Nov. 17, 1988, now abandoned, of common assignee herewith. In still another embodiment, the antigen may be adsorbed directly onto the membrane, and the membrane containing antigen subsequently treated with the inert protein to fill all unoccupied binding sites.

The membrane having ligand bound thereto may be treated with a solution of the tracer. The tracer may be an antiligand, hereinafter referred to as the detection antiligand, conjugated to urease wherein the assay is performed by the conventional sandwich or half sandwich technique. The preferred detection antiligand is an antibody which binds to antigen captured on the membrane and thereby affixes urease to the membrane surface in direct proportion to the quantity of antigen in the sample. Alternatively, the urease may be conjugated by conventional methods to a binder such as biotin, avidin and streptavidin and the latter bound to the antiligand.

The assay may also be performed by competitive assay, in which case the tracer may be the ligand conjugated to urease or to a conjugate of urease with biotin, avidin or streptavidin. In this format, the ligand and tracer compete for antiligand binding sites, and the urease becomes affixed to the membrane surface in inverse proportion to the quantity of ligand in the sample. Competitive assay may also be carried out with a tracer comprising urease linked to a hapten which has been used to raise the detection antibody, preferably a monoclonal antibody.

Conjugation of enzymes, such as urease, or enzyme conjugates with biotin, avidin or streptavidin to antigens or antibodies is well-known in the art and deemed to be within the purview of one skilled in the art with no further detail.

The membrane having urease affixed thereto may be treated with the substrate composition of the invention. The composition may include at least three components which interact consecutively leading to a colored insoluble product. The first component of the composition is a compound converted by the urease to a pH-raising substance. Suitable compounds as known in the art are urea, substituted ureas such as, for example, N-methylurea and semicarbazide, and simple amides such as formamide and acetamide. Urease cleaves these compounds to ammonia which raises the pH of the assay medium. The preferred first component is urea.

The second component of the substrate composition may be a pH dependent reducing agent for the third component. Suitable second components are indoxyl and, preferably, ascorbic acid. The second component does not reduce the third component, a tetrazolium salt, at low pH. Liberation of ammonia by the action of urease on the first component, however, raises the pH sufficiently to trigger the reduction of the tetrazolium salt to a colored, insoluble formazan. Reduction of tetrazolium salts to formazans is well-known in the art. Representative suitable tetrazolium salts are iodonitrotetrazolium violet and nitrobluetetrazolium chloride, although others are well-known to those skilled in the art.

Thus, in the preferred sandwich assay of the invention, ligand in the sample is captured by the antiligand coated onto the membrane. Captured ligand binds to the tracer whereby urease becomes affixed to the membrane. Urease affixed to the membrane converts the urea in the substrate composition to ammonia. The ammonia raises the pH to a level at which the ascorbic acid reduces the tetrazolium salt to the formazan. Accordingly, in the sandwich assay format, the appearance of color on the membrane is indicative of ligand in the sample.

In a competitive assay, ligand in the sample competes with tracer for binding to the antiligand. Thus, in this assay configuration, tracer, and therefore, urease, becomes affixed to the membrane in inverse proportion to the concentration of ligand. Accordingly, in a competitive assay, absence of colored formazan is indicative of ligand in the sample.

It is evident that the method of the invention may be used to assay for urea. For this embodiment of the invention, urease may be adsorbed on the membrane and a solution containing an unknown amount of urea, ascorbate and a tetrazolium salt may then be passed through the membrane. Urea in the unknown causes a spot to appear on the membrane. The color may be compared to standards containing known quantities of urea to quantitate the urea.

The following examples are provided to further describe the invention but are in no way to be considered as limitative of the invention.

EXAMPLE I

Detection of Urease Using Sodium Ascorbate/Iodonitrotetrazolium Violet (Biodyne C Membrane)

A membrane filter stack was assembled with the following configuration:

Top Layer—Three micron Biodyne ® C Membrane, (Pall, Glen Cove, N.Y., #BIA0030HC5). Precoated by immersion in phosphate buffered saline containing 0.3% casein for 30 minutes at ambient temperature.

Next Layer—Non-woven rayon sheet (Schleicher and Schuell, Keene, N.H.; #5-S)

Bottom Layer—Cellulose absorbent pads (2) (Filtration Sciences, Mount Holly Springs, Pa.; #ED 320-200)

The membrane layers were encased in a plastic holder which includes a receiving well formed above the top layer. Within this well was fitted a flow restriction insert which has an aperture more narrow than the receiving well and sits flush against the top membrane.

A solution of urease-biotin conjugate in TEOA buffer (150 $\mu$l, 0.1 M triethanolamine, 1 mM EDTA, pH 7.6) was added through the restriction insert to produce a triangular pattern of adsorbed urease-biotin conjugate on the membrane. After one minute, the insert was removed and the membrane washed with TEOA buffer (200 $\mu$l). An aqueous solution of iodonitrotetrazolium violet (200 $\mu$l, 0.2 mg/ml) was added, followed by urease substrate (200 $\mu$l, 25 mM urea, 1 mM EDTA, 20 mM sodium ascorbate, pH 5.0). After 10,20 and 30 minutes, stop buffer (400 $\mu$l, 150 mM sodium citrate, pH 3.0) was added and the membrane color determined using a Gretag reflectometer (magenta setting). This color was observed as a triangular pattern corresponding to adsorbed urease-biotin conjugate. Samples without added urease showed no triangular pattern on the membrane.

The relationship between the time of incubation and the limit of urease detection is given in the FIGURE.

EXAMPLE II

Detection of Urease Using Sodium Ascorbate/Nitrobluetetrazolium Chloride (Biodyne C Membrane)

The procedure in Example I was followed except for the substitution of aqueous iodonitrotetrazolium violet by nitrobluetetrazolium chloride (300 µl, 0.165 mg/ml, 0.5% methanol). After twelve minutes, the membrane color was determined used a Gretag reflectometer (black setting). The detection limit for urease-biotin was 10 ng/test. Membranes without added urease showed no triangular pattern.

EXAMPLE III

Detection of Urease Using Indoxyl/Nitrobluetetrazolium Chloride (Biodyne C Membrane)

Urease-biotin conjugate was adsorbed onto Biodyne C membranes as described in Example I. The insert was removed and the sample washed with TEOA buffer (200 µl). Urease substrate solution (25 mM urea, 1 mM, EDTA, 1 mM indoxyl butyrate) was treated with rabbit liver esterase (5.3 µg/ml) to generate indoxyl from indoxylbutyrate. The solution was mixed briefly and added to the device. After twelve minutes, stop buffer was added and the membrane color was read using a Gretag reflectometer (black setting). The detection limit for urease-biotin was 10 ng/test. Color was observed only where the urease-biotin conjugate was bound to the membrane.

EXAMPLE IV

Assay for Urea Using Tetrazolium Salt Reduction

Devices are prepared as described in Example I. A solution of urease in TEOA buffer is adsorbed onto the Biodyne C membrane. An aqueous solution of iodonitrotetrazolium violet (200 uL, 0.2 mg/mL) is added and allowed to flow through the device. A sample containing an unknown quantity of urea is passed through the membrane and standards having known concentrations of urea in substrate buffer (1 mM EDTA, 20 mM sodium ascorbate) are applied to other membranes having the same amount of adsorbed urease. After five minutes the intensity of color in the unknown is measured with a reflectometer and correlated to the amount of urea present in the standards. This correlation is in turn used to determine the concentration of urea present in unknown samples assayed by the above method.

What is claimed is:

1. A urease substrate composition comprising;
    a) a first component selected from the group consisting of urea, substituted ureas and simple amides;
    b) a second component selected from the group consisting of indoxyl, indoxyl butyrate, sodium ascorbate and ascorbic acid, and;
    c) optionally a tetrazolium salt;

wherein the composition has an acidic pH which prevents reduction of the tetrazolium salt by the second component, if the tetrazolium salt is present, and wherein the first and second components are present in amounts such that cleavage of the first component by urease increases the pH and allows the second component to reduce the tetrazolium salt if present to an insoluble formazan.

2. The composition of claim 1 wherein the first component is selected from the group consisting of urea, N-methylurea, semicarbazide, acetamide and formamide.

3. The composition of claim 2 wherein the first component is about 25 mM urea and the second component is about 20 mM sodium ascorbate.

4. The composition of claim 3 wherein the tetrazolium salt is selected from the group consisting of iodonitrotetrazolium violet and nitrobluetetrazolium chloride.

5. The composition of claim 1 wherein the first component is about 25 mM urea and the second component is about 1 mM indoxyl butyrate.

6. The composition of claim 5 which comprises a tetrazolium salt selected from the group consisting of iodonitrotetrazolium violet and nitrobluetetrazolium chloride.

7. The composition of claim 1 which comprises a tetrazolium salt.

8. The composition of claim 7 wherein the tetrazolium salt is selected from the group consisting of iodonitrotetrazolium violet and nitrobluetetrazolium chloride.

* * * * *